US011866663B1

(12) United States Patent
Al-Herz et al.

(10) Patent No.: US 11,866,663 B1
(45) Date of Patent: Jan. 9, 2024

(54) MULTI-ZONE CATALYTIC CRACKING OF CRUDE OILS

(71) Applicant: Saudi Arabian Oil Company, Dhahran (SA)

(72) Inventors: Mansour Ali Al-Herz, Al-Ahsa (SA); Ali Al Jawad, Al-Qatif (SA); Qi Xu, Dhahran (SA); Aaron Akah, Dhahran (SA); Musaed Salem Al-Ghrami, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 18/163,556

(22) Filed: Feb. 2, 2023

(51) Int. Cl.
*C10G 69/04* (2006.01)
*C07C 4/06* (2006.01)

(52) U.S. Cl.
CPC ............... *C10G 69/04* (2013.01); *C07C 4/06* (2013.01); *C10G 2300/104* (2013.01); *C10G 2300/1044* (2013.01); *C10G 2300/301* (2013.01); *C10G 2300/302* (2013.01); *C10G 2300/308* (2013.01); *C10G 2400/20* (2013.01); *C10G 2400/22* (2013.01)

(58) Field of Classification Search
CPC ............. C10G 69/00; C10G 2300/202; C10G 2300/205; C10G 2300/301; C10G 2300/302; C10G 2300/308; C10G 2400/20
See application file for complete search history.

(56) References Cited

U.S. PATENT DOCUMENTS

| | | |
|---|---|---|
| 5,318,695 A | 6/1994 | Eberly et al. |
| 7,019,187 B2 | 3/2006 | Powers |

(Continued)

FOREIGN PATENT DOCUMENTS

| | | |
|---|---|---|
| CN | 1557915 A | 12/2004 |
| WO | 2009073436 A2 | 6/2009 |

(Continued)

OTHER PUBLICATIONS

Chen et al., "Novel Propylene Production Route: Utilizing Hydrotreated Shale Oil as Feedstock via Two-Stage Riser Catgalytic Cracking", Energy & Fuels, vol. 29, pp. 7190-7195, 2015.

(Continued)

*Primary Examiner* — Ellen M Mcavoy
*Assistant Examiner* — Chantel Graham
(74) *Attorney, Agent, or Firm* — DINSMORE & SHOHL LLP (57) ABSTRACT

Embodiments of the present disclosure are directed to a method of processing a hydrocarbon feed includes fractionating the hydrocarbon feed into a light stream and a heavy stream, hydrotreating the heavy stream to form a hydrotreated heavy stream, combining the light stream and the hydrotreated heavy stream to form a upgraded feed stream, and feeding the upgraded feed stream to a single Fluid Catalytic Cracking (FCC) reaction zone, thereby producing a product stream comprising light olefins. The light stream may comprise hydrocarbons boiling at less than 540° C. and the heavy stream may comprise hydrocarbons boiling at greater than 540° C. The FCC reaction zone may be operated in a down-flow configuration and the FCC may be operated under high severity conditions.

17 Claims, 1 Drawing Sheet

(56) References Cited

U.S. PATENT DOCUMENTS

| | | |
|---|---|---|
| 9,096,806 B2 | 8/2015 | Abba et al. |
| 9,290,705 B2 | 3/2016 | Bourane et al. |
| 9,764,314 B2 | 9/2017 | Al-Alloush et al. |
| 10,889,768 B2 | 1/2021 | Bourane et al. |
| 10,954,457 B2 | 3/2021 | Al-Herz et al. |
| 11,230,672 B1 | 1/2022 | Al Herz et al. |
| 2005/0211603 A1 | 9/2005 | Guillaume et al. |
| 2008/0223754 A1* | 9/2008 | Subramanian ......... C10G 69/04 196/14.52 |
| 2011/0083996 A1 | 4/2011 | Shafi et al. |
| 2013/0248421 A1 | 9/2013 | Abba et al. |
| 2014/0275673 A1 | 9/2014 | Long et al. |
| 2019/0316047 A1 | 10/2019 | Al-Majnouni et al. |
| 2021/0363433 A1* | 11/2021 | Fathi ...................... C10G 31/06 |

FOREIGN PATENT DOCUMENTS

| | | |
|---|---|---|
| WO | 2010009077 A2 | 1/2010 |
| WO | 2010009082 A1 | 1/2010 |
| WO | 2010009089 A2 | 1/2010 |
| WO | 2013142563 A2 | 9/2013 |

OTHER PUBLICATIONS

Corma et al., "Crude oil to chemicals: light olefins from crude oil", Catalysis Science & Technology, vol. 7, pp. 12-46, 2017.

Usman et al., "Catalytic cracking of crude oil to light olefins and naphtha: Experimental and kinetic modeling", Chemical Engineering Research and Design, vol. 120, pp. 121-137, 2017.

* cited by examiner

MULTI-ZONE CATALYTIC CRACKING OF CRUDE OILS

BACKGROUND

Field

The present disclosure relates to processes for processing petroleum-based materials and, in particular, processes for cracking hydrocarbon feeds to produce light olefins.

Technical Background

The worldwide increasing demand for light chemical intermediates remains a major challenge for many integrated refineries. In particular, the production of some valuable light olefins, such as ethylene and propylene, has attracted increased attention as pure olefin streams are considered the building blocks for polymer synthesis. The production of light olefins depends on several process variables, such as the feed type, operating conditions, and the type of catalyst. Despite the options available for producing a greater yield of propylene and light olefins, intense research activity in this field is still being conducted.

Light olefins are typically produced through thermal cracking (or steam pyrolysis) of petroleum gases and distillates, such as naphtha, kerosene, or gas oil. Light olefins may also be produced through fluid catalytic cracking processes. Typical hydrocarbon feeds for fluid catalytic cracking processes range from hydrocracked bottoms to heavy feed fractions such as vacuum gas oil and atmospheric residue; however, these hydrocarbon feeds are limited in supply and at least in part, due to limitations of processes used in fluid catalytic cracking processes.

SUMMARY

Accordingly, there is an ongoing need for integrated processes that can produce intermediate chemical compounds from hydrocarbon feeds, such as crude oil. The processes of the present disclosure include fractionating a hydrocarbon feed into two streams, contacting the heavy stream with one or more hydrotreating catalysts to form a hydrotreated effluent, and contacting the hydrotreated effluent and the light streams with an FCC catalyst composition. In particular, the processes of the present disclosure include fractionating the hydrocarbon feed into a light stream and a heavy stream; hydrotreating the heavy stream; combining the light stream and the hydrotreated heavy stream to form an upgraded feed stream, and introducing the upgraded feed stream to a single fluidized catalytic cracking (FCC) reaction zone.

According to one embodiment of the present disclosure, a method of processing a hydrocarbon feed includes fractionating the hydrocarbon feed into a light stream and a heavy stream, hydrotreating the heavy stream to form a hydrotreated heavy stream, combining the light stream and the hydrotreated heavy stream to form a upgraded feed stream, and feeding the upgraded feed stream to a single Fluid Catalytic Cracking (FCC) reaction zone, thereby producing a product stream comprising light olefins. The light stream may comprise hydrocarbons boiling at less than 540° C. and the heavy stream may comprise hydrocarbons boiling at greater than 540° C. The FCC reaction zone may be operated in a down-flow configuration and the FCC may be operated under high severity conditions.

Additional features and advantages of the embodiment of the present disclosure will be set forth in the detailed description that follows and, in part, will be readily apparent to a person of ordinary skill in the art from the detailed description or recognized by practicing the embodiments of the present disclosure.

BRIEF DESCRIPTION OF THE DRAWING

The following detailed description of the present disclosure may be better understood when read in conjunction with the following drawing in which.

Figure 1:
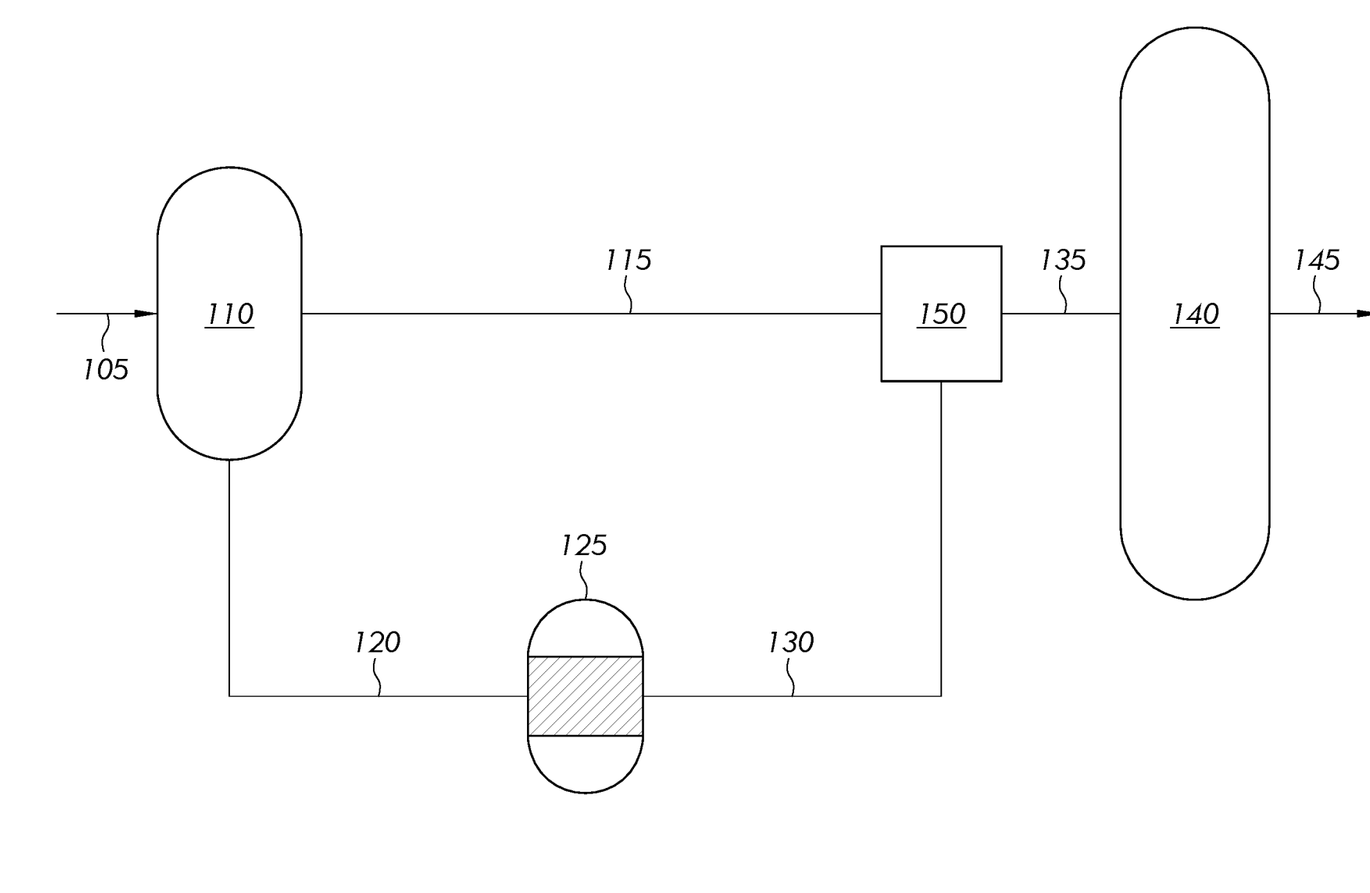
FIG. 1 schematically depicts a generalized flow diagram of a system for converting a hydrocarbon feed to produce olefins, according to one or more aspects of the present disclosure.

When describing the simplified schematic illustration of FIG. 1, the numerous valves, temperature sensors, electronic controllers, and the like, which may be used and are well known to a person of ordinary skill in the art, are not included. Further, accompanying components that are often included in systems such as those depicted in FIG. 1, such as air supplies, heat exchangers, surge tanks, and the like are also not included. However, a person of ordinary skill in the art understands that these components are within the scope of the present disclosure.

Reference will now be made in greater detail to various aspects, some of which are illustrated in the accompanying drawings.

DETAILED DESCRIPTION

The present disclosure is directed to processes and catalysts for upgrading hydrocarbon feeds, such as crude oil, through hydrotreating and fluidized catalytic cracking (FCC) to produce greater value chemical products and intermediates, such as but not limited to light olefins, aromatic compounds, and combinations thereof. The processes and FCC catalyst compositions of the present disclosure can enable efficient cracking of feed streams, such as those comprising crude oil, by taking advantage of hydrotreating and FCC, such as a down-flow FCC.

Definitions

As used in the present disclosure, the term "API" refers to the American Petroleum Institute.

As used in the present disclosure, the term "ASTM" refers to the American Society for Testing and Materials As used in the present disclosure, the term "cracking" refers to a chemical reaction where a molecule having carbon-carbon bonds is broken into more than one molecule by the breaking of one or more of the carbon-carbon bonds; where a compound including a cyclic moiety, such as an aromatic, is converted to a compound that does not include a cyclic moiety; or where a molecule having carbon-carbon double bonds are reduced to carbon-carbon single bonds. As used in the present disclosure, the term "catalytic cracking" refers to cracking conducted in the presence of a catalyst. Some catalysts may have multiple forms of catalytic activity, and calling a catalyst by one particular function does not render that catalyst incapable of being catalytically active for other functionality.

As used in the present disclosure, the term "catalyst" refers to any substance that increases the rate of a specific chemical reaction, such as cracking reactions.

As used in the present disclosure, the term "crude oil" refers to a mixture of petroleum liquids and gases, including impurities, such as sulfur-containing compounds, nitrogen-containing compounds, and metal compounds, extracted directly from a subterranean formation or received from a desalting unit without having any fractions, such as naphtha, separated by distillation.

As used in the present disclosure, the term "naphtha" refers to an intermediate mixture of hydrocarbon-containing materials derived from crude oil refining and having atmospheric boiling points from 36 degrees Celsius (° C.) to 220° C. Naphtha may comprise light naphtha comprising hydrocarbon-containing materials having atmospheric boiling points from 36° C. to 80° C., intermediate naphtha comprising hydrocarbon-containing materials having atmospheric boiling points from 80° C. to 140° C., and heavy naphtha comprising hydrocarbon-containing materials having atmospheric boiling points from 140° C. to 200° C. Naphtha may comprise paraffinic, naphthenic, and aromatic hydrocarbons having from 4 carbon atoms to 11 carbon atoms.

As used in the present disclosure, the term "directly" refers to the passing of materials, such as an effluent, from a first component of the system to a second component of the system without passing the materials through any intervening components or systems operable to change the composition of the materials. Similarly, the term "directly" also refers to the introducing of materials, such as a feed, to a component of the system without passing the materials through any preliminary components operable to change the composition of the materials. Intervening or preliminary components or systems operable to change the composition of the materials can include reactors and separators, but are not generally intended to include heat exchangers, valves, pumps, sensors, or other ancillary components required for operation of a chemical process. Further, combining two streams together upstream of the second component instead of passing each stream to the second component separately is also not considered to be an intervening or preliminary component operable to change the composition of the materials.

As used in the present disclosure, the terms "downstream" and "upstream" refer to the positioning of components or systems relative to a direction of flow of materials through the system. For example, a second component may be considered "downstream" of a first component if materials flowing through the system encounter the first component before encountering the second component. Likewise, the first component may be considered "upstream" of the second component if the materials flowing through the system encounter the first component before encountering the second component.

As used in the present disclosure, the term "effluent" refers to a stream that is passed out of a reactor, a reaction zone, or a separator following a particular reaction or separation. Generally, an effluent has a different composition than the stream that entered the reactor, reaction zone, or separator. It should be understood that when an effluent is passed to another component or system, only a portion of that effluent may be passed. For example, a slipstream may carry some of the effluent away, meaning that only a portion of the effluent may enter the downstream component or system. The terms "reaction effluent" and "reactor effluent" particularly refer to a stream that is passed out of a reactor or reaction zone.

As used in the present disclosure, the term "high-severity conditions" refers to operating conditions of a fluid catalytic cracking system, such as the FCC system, that include temperatures greater than or equal to 580° C., or from 580° C. to 750° C., a catalyst to oil ratio greater than or equal to 1:1, or from 1:1 to 60:1, and a residence time of less than or equal to 60 seconds, or from 0.1 seconds to 60 seconds, each of which conditions may be more severe than typical operating conditions of fluid catalytic cracking systems.

As used in the present disclosure, the term "catalyst to oil ratio" or "CTO weight ratio" refers to the weight ratio of a catalyst to a process stream comprising hydrocarbons.

The term "residence time" refers to the amount of time that reactants are in contact with a catalyst, at reaction conditions, such as at the reaction temperature.

As used in the present disclosure, the term "reactor" refers to any vessel, container, conduit, or the like, in which a chemical reaction, such as catalytic cracking, occurs between one or more reactants optionally in the presence of one or more catalysts. A reactor can include one or a plurality of "reaction zones" disposed within the reactor. The term "reaction zone" refers to a region in a reactor where a particular reaction takes place.

As used in the present disclosure, the terms "separation unit," and "separator" refer to any separation device(s) that at least partially separates one or more chemical constituents in a mixture from one another. For example, a separation system selectively separates different chemical constituents from one another, forming one or more chemical fractions. Examples of separation systems include, without limitation, distillation columns, fractionators, flash drums, knock-out drums, knock-out pots, centrifuges, filtration devices, traps, scrubbers, expansion devices, membranes, solvent extraction devices, high-pressure separators, low-pressure separators, or combinations of these. The separation processes described in the present disclosure may not completely separate all of one chemical constituent from all of another chemical constituent. Instead, the separation processes described in the present disclosure "at least partially" separate different chemical constituents from one another and, even if not explicitly stated, separation can include only partial separation.

As used herein, the term "light olefins" means olefinic (comprising at least one double bond) hydrocarbons with from 2 to 4 carbon atoms. For example, light olefins may comprise ethylene, propylene, and butylene.

It should further be understood that streams may be named for the components of the stream, and the component for which the stream is named may be the major component of the stream (such as comprising from 50 wt. %, from 70 wt. %, from 90 wt. %, from 95 wt. %, from 99 wt. %, from 99.5 wt. %, or from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "heavy oil stream" passing to a first system component or from a first system component to a second system component should be understood to equivalently disclose "heavy oil" passing to the first system component or passing from a first system component to a second system component.

The composition of feed streams and processing variables of FCC systems play a significant role in the reaction yields and heat balance within the systems. Conventional FCC systems and processes can require costly refining to produce suitable feed streams. Such additional costly refining can include separating and processing of one or more fractions of a hydrocarbon feedstock before introducing the refined conventional feed into the FCC system. These additional processing steps are energy intensive and reduce the amount of viable feed from an existing hydrocarbon source. Previous systems and methods have been developed to convert crude oil to greater value chemical products and intermediates directly through catalytic cracking to attempt to overcome these limitations, such as by reducing or eliminating the processing steps needed to produce a suitable hydrocarbon feed before introduction into an FCC system. However, contaminants, metals, or both present in heavy hydrocarbon feeds, such as crude oil, can deactivate the catalyst, resulting in decreased yields and increased production costs.

EMBODIMENTS

Accordingly, embodiments of the present disclosure are directed to an integrated processes for converting crude oil directly to greater value chemical products and intermediates, such as but not limited to olefins and aromatic compounds, through a combination of hydrotreating and FCC using the reaction configurations specified herein.

Referring now to FIG. 1, a method 100 of processing a hydrocarbon feed 105 may comprise fractionating 110 the hydrocarbon feed 105 into a light stream 115 and a heavy stream 120. The method 100 may further comprise hydrotreating 125 the heavy stream 120 to form a hydrotreated heavy stream 130. The light stream 115 and the hydrotreated heavy stream 130 may be combined to form a combined feed stream 135. The combined feed stream 135 may be fed to a single FCC reaction zone 140, thereby producing a product stream 145 comprising light olefins.

The Hydrocarbon Feed

The hydrocarbon feed 105 to the present method 100 may be a crude oil, such as a whole crude oil. The "crude oil" may be a raw hydrocarbon which has not been previously processed, such as through one or more of distillation, cracking, hydrotreating, desalting, or dehydration. In embodiments, the crude oil may have undergone at least some processing, such as desalting, solids separation, scrubbing, or combinations of these, but has not been subjected to distillation. For instance, the crude oil may be a de-salted crude oil that has been subjected to a de-salting process. In embodiments, crude oil may not have undergone pretreatment, separation (such as distillation), or other operation that changes the hydrocarbon composition of the crude oil prior to introducing the crude oil to the method 100. As used herein, the "hydrocarbon composition" of the crude oil refers to the composition of the hydrocarbon constituents of the crude oil and does not include entrained non-hydrocarbon solids, salts, water, or other non-hydrocarbon constituents.

The hydrocarbon feed 105, such as a crude oil, may have an American Petroleum Institute (API) gravity of from 25 to 55. For example, the hydrocarbon feed 105 may have an API gravity from 45 to 55, from 50 to 52, from 25 to 35, from 27 to 29, from 30 to 32, from 32 to 34, from 27 to 32, or any subset thereof. The hydrocarbon feed 105 may have a density of greater than 0.8 grams per milliliter (g/ml), greater than 0.82 g/ml, greater than 0.84 g/ml, 0.86 g/ml, 0.88 g/ml, greater than 0.90 g/ml, greater than 0.91 g/ml, from 0.8 g/ml to 1.0 g/ml, from 0.84 to 0.96 g/ml, from 0.86 g/ml to 0.93 g/ml, from 0.88 g/ml to 0.92 g/ml, from 0.9 g/ml to 0.92 g/ml, or any subset thereof, at a temperature of 15 degrees Celsius. According to some embodiments, the hydrocarbon feed 105 may be an Arab heavy crude oil, an Arab medium crude oil, an Arab light crude oil, or an Arab super light crude oil.

The hydrocarbon feed 105 may have an initial boiling point from 30° C. to 50° C. For example, the hydrocarbon feed 105 may have an initial boiling point from 30° C. to 45° C., from 30° C. to 40° C., from 30° C. to 35° C., from 35° C. to 50° C., from 40° C. to 50° C., from 45° C. to 50° C., or any subset thereof. The initial boiling point may be determined according to standard test method ASTM D7169.

The hydrocarbon feed 105 may have an end boiling point (also referred to herein as "EBP" and "FBP") greater than 720 degrees Celsius. For example, the hydrocarbon feed 105 may have an end boiling point greater than 740° C., greater than 760° C., greater than 780° C., greater than 800° C., greater than 850° C., greater than 900° C., greater than 950° C., or greater than 1000° C. The hydrocarbon feed 105 may have an end boiling point less than 2000° C., less than 1800° C., less than 1600° C., less than 1400° C., less than 1200° C., less than 1000° C., less than 900° C., less than 800° C., less than 750° C., or any subset thereof. The end boiling point may be determined according to standard test method ASTM D7169.

At least 50 weight percent of the hydrocarbon feed 105 may have a boiling point temperature greater than or equal to 300° C. For example, the hydrocarbon feed 105 may have a 50 wt. % boiling point temperature from 300° C. to 500° C., from 300° C. to 475° C., from 300° C. to 450° C., from 300° C. to 425° C., from 300° C. to 400° C., from 300° C. to 375° C., 350° C. to 500° C., from 350° C. to 475° C., from 350° C. to 450° C., from 350° C. to 425° C., from 350° C. to 400° C., from 350° C. to 375° C., 375° C. to 500° C., from 375° C. to 475° C., from 375° C. to 450° C., from 375° C. to 425° C., from 375° C. to 400° C., or any subset thereof. The 50 weight percent boiling temperature may be determined according to standard test method ASTM D7169.

The hydrocarbon feed 105 may have a nitrogen concentration of less than or equal to 5000 parts per million by weight (ppmw). For example, the hydrocarbon feed 105 may have a nitrogen concentration of less than 4500 ppmw, less than 4000 ppmw, less than 3500 ppmw, less than 3000 ppmw, less than 2500 ppmw, less than 2000 ppmw, from 1000 ppmw to 5000 ppmw, from 1000 to 4000 ppmw, from 1000 ppmw to 3000 ppmw, from 1000 ppmw to 2000 ppmw, or any subset thereof. The nitrogen concentration of the hydrocarbon feed 105 may be determined according to standard test method ASTM D4629.

The hydrocarbon feed 105 may have a concentration of paraffin compounds of less than 50 wt. % per unit weight of the hydrocarbon feed 105. For example, the hydrocarbon feed 105 may have a concentration of paraffin compounds of less than or equal to 40 wt. %, less than or equal to 35 wt. %, less than or equal to 30 wt. %, less than or equal to 25 wt. %, less than or equal to 20 wt. %, less than or equal to 15 wt. %, less than or equal to 10 wt. %, or even less than or equal to 5 wt. %, per unit weight of the hydrocarbon feed 105. In embodiments, the hydrocarbon feed 105 may have a concentration of paraffin compounds of from 5 wt. % to less than 50 wt. %, from 5 wt. % to 40 wt. %, from 5 wt. % to 35 wt. %, from 5 wt. % to 30 wt. %, from 5 wt. % to 25 wt. %, from 5 wt. % to 20 wt. %, from 10 wt. % to less than 50 wt. %, from 10 wt. % to 40 wt. %, from 10 wt. % to 35 wt. %, from 10 wt. % to 30 wt. %, from 10 wt. % to 25 wt. %, or even from 10 wt. % to 20 wt. % per unit weight of the hydrocarbon feed 105. The paraffin content of the hydrocarbon feed 105 may be determined according to ASTM 5443.

The hydrocarbon feed 105 may have a concentration of aromatic compounds of greater than or equal to 20 wt. %, per unit weight of the hydrocarbon feed 105. For example, the hydrocarbon feed 105 may have a concentration of aromatic compounds of greater than or equal to 30 wt. %, greater than or equal to 40 wt. %, or even greater than or equal to 50 wt. % per unit weight of the hydrocarbon feed 105, as determined according to ASTM 5443. In embodiments, the hydrocarbon feed 105 may have a concentration of aromatic compounds of from 20 wt. % to 90 wt. %, from 20 wt. % to 80 wt. %, from 20 wt. % to 70 wt. %, from 30 wt. % to 90 wt. %, from 30 wt. % to 80 wt. %, from 30 wt. % to 70 wt. %, from 40 wt. % to 90 wt. %, from 40 wt. % to 80 wt. %, from 40 wt. % to 70 wt. %, from 50 wt. % to 90 wt. %, from 50 wt. % to 80 wt. %, from 50 wt. % to 70 wt. %, or any subset thereof, per unit weight of the hydrocarbon feed 105.

The hydrocarbon feed 105 may have a concentration of naphthenes of greater than or equal to 25 wt. % per unit weight of the hydrocarbon feed 105. For example, the hydrocarbon feed 105 may have a concentration of naphthenes greater than or equal to 27 wt. % per unit weight of the hydrocarbon feed 105, as determined according to ASTM 5443. In embodiments, the hydrocarbon feed 105 can have a concentration of naphthenes of from 25 wt. % to 60 wt. %, from 25 wt. % to 50 wt. %, from 25 wt. % to 40 wt. %, from 25 wt. % to 35 wt. %, from 27 wt. % to 60 wt. %, from 27 wt. % to 50 wt. %, from 27 wt. % to 40 wt. %, from 27 wt. % to 35 wt. %, or any subset thereof per unit weight of the hydrocarbon feed 105.

In some embodiments, the hydrocarbon feed 105 may be a topped crude oil. As used in the present disclosure, the term "topped crude oil" refers to crude oil from which lesser boiling constituents have been removed through distillation, such as constituents having boiling point temperatures less than 180° C. or even less than 160° C. The hydrocarbon feed 105 may comprise, consist of, or consist essentially of a topped crude oil, which has greater than or equal to 95%, greater than or equal to 98%, or even greater than or equal to 99% constituents having boiling point temperatures greater than or equal to 160° C. or greater than or equal to 180° C., depending on the cut point temperature of the topping unit.

Fractionating

Fractionating 110 the hydrocarbon feed 105 to produce the light stream 115 and the heavy stream 120 may occur in any separator. For example, the fractionating 110 step may include, without limitation, distillation columns, fractionators, flash drums, knock-out drums, knock-out pots, centrifuges, filtration devices, traps, scrubbers, expansion devices, membranes, solvent extraction devices, high-pressure separators, low-pressure separators, or combinations of these.

The Light Stream

Fractionating 110 the hydrocarbon feed 105 may produce a light stream 115. The light stream 115 may comprise hydrocarbons boiling at less than or equal to 540° C. At least 50 wt. %, at least 60 wt. %, at least 70 wt. %, at least 80 wt. %, at least 90 wt. %, at least 95 wt. %, at least 99 wt. %, or even at least 99.9 wt. % of the hydrocarbons in the light stream 115 may boil at less than or equal to 540° C., based on the total weight of hydrocarbons in the light stream 115.

The light stream 115 may comprise at least 50 wt. % of all hydrocarbons with a boiling point of less than or equal to 540° C., which were originally in the hydrocarbon feed 105. For example, the light stream 115 may comprise at least 75 wt. %, at least 80 wt. %, at least 90 wt. %, at least 95 wt. %, or at least 99 wt. % of all hydrocarbons with a boiling point of less than or equal to at less than or equal to 540° C. which were originally in the hydrocarbon feed 105. In some embodiments, the light stream 115 may comprise at least 75 wt. %, at least 80 wt. %, at least 90 wt. %, at least 95 wt. %, or at least 99 wt. % of all hydrocarbons with a boiling point of from 25° C. to 540° C., from 35° C. to 540° C., or from 45° C. to 540° C. which were originally in the hydrocarbon feed 105.

The light stream 115 may comprise less than 5 wt. % sulfur, based on the total weight of hydrocarbons in the light stream 115. For example, the light stream 115 may comprise less than 2.5 wt. %, less than 1 wt. %, less than 0.5 wt. %, less than 0.1 wt. %, or even less than 0.01 wt. % sulfur, based on the total weight of hydrocarbons in the light stream 115.

The light stream 115 may comprise less than 50 ppm of nitrogen. For example, the light stream 115 may comprise less than 25 ppm, less than 15 ppm, less than 10 ppm, or even less than 5 ppm of nitrogen.

The light stream 115 may comprise less than 5 ppm nickel. For example, the light stream 115 may comprise less than 2.5 ppm, less than 2 ppm, less than 1 ppm, or even less than 0.1 ppm of nickel.

The light stream 115 may comprise less than 5 ppm vanadium. For example, the light stream 115 may comprise less than 2.5 ppm, less than 2 ppm, less than 1 ppm, or even less than 0.1 ppm of vanadium.

The light stream 115 may comprise from 50 wt. % to 99 wt. % of paraffins, based on the total weight of hydrocarbons in the light stream 115. For example, the light stream 115 may comprise from 60 wt. % to 90 wt. %, from 60 wt. % to 80 wt. %, from 65 wt. % to 75 wt. %, from 70 wt. % to 75 wt. %, or any subset thereof, of paraffins, based on the total weight of hydrocarbons in the light stream 115.

The light stream 115 may comprise from 1 wt. % to 30 wt. % of naphthenes, based on the total weight of hydrocarbons in the light stream 115. For example, the light stream 115 may comprise from 5 wt. % to 25 wt. %, from 10 wt. % to 20 wt. %, from 12.5 wt. % to 17.5 wt. %, or any subset thereof, of naphthenes, based on the total weight of hydrocarbons in the light stream 115.

The light stream 115 may comprise from 1 wt. % to 25 wt. % of aromatics, based on the total weight of hydrocarbons in the light stream 115. For example, the light stream 115 may comprise from 5 wt. % to 20 wt. %, from 10 wt. % to 15 wt. %, or any subset thereof, of aromatics, based on the total weight of hydrocarbons in the light stream 115.

The Heavy Stream

Fractionating 110 the hydrocarbon feed 105 may produce a heavy stream 120. The heavy stream 120 may comprise hydrocarbons boiling at greater than 540° C. For example, at least 50 wt. %, at least 60 wt. %, at least 70 wt. %, at least 80 wt. %, at least 90 wt. %, at least 95 wt. %, at least 99 wt. %, or even at least 99.9 wt. % of the heavy stream 120 may comprise hydrocarbons boiling at greater than from 540° C., based on the total weight of hydrocarbons in the heavy stream 120.

Without being limited by theory, the cut points for the heavy stream 120 were selected to cluster metal contaminants (such as Ni and V) and poly-aromatics in the heavy stream 120 which is subjected to hydrotreatment.

The heavy stream 120 may comprise at least 50 wt. %, at least 75 wt. %, at least 90 wt. %, at least 95 wt. %, at least 99 wt. %, or even at least 99.9 wt. % of all hydrocarbons boiling at a temperature of at least 540° C., which were originally in the hydrocarbon feed 105, based on the total weight of hydrocarbons in the hydrocarbon feed 105.

The heavy stream 120 may comprise less than 15 wt. % of sulfur, based on the total weight of hydrocarbons in the heavy stream 120. For example, the heavy stream 120 may comprise less than 12.5 wt. %, less than 10 wt. %, less than 7.5 wt. %, or less than 5 wt. %, from 1 wt. %, to 15 wt. %, from 1 wt. %, to 10 wt. %, from 1 wt. %, to 5 wt. %, or any subset thereof, of sulfur, based on the total weight of hydrocarbons in the heavy stream 120.

The heavy stream 120 may comprise less than 2500 ppm of nitrogen, such as less than 2000 ppm, less than 1500 ppm, less than 1000 ppm, less than 1750 ppm, less than 1600 ppm nitrogen. The heavy stream 120 may comprise at least 1000 ppm nitrogen, such as at least 1250, at least 1500, from 1000 ppm to 2500 ppm, from 1000 ppm to 2000 ppm, from 1250 ppm to 1750 ppm, from 1500 to 1750 ppm, or any subset thereof, of nitrogen.

The heavy stream 120 may comprise less than 1000 ppm nickel. For example, the heavy stream 120 may comprise less than 750 ppm, less than 500 ppm, less than 250 ppm, less than 100 ppm, less than 75 ppm, less than 50 ppm, less than 25 ppm, from 20 to 1000 ppm, from 20 to 100 ppm, or any subset thereof of nickel.

The heavy stream 120 may comprise less than 1000 ppm vanadium. For example, the heavy stream 120 may comprise less than 750 ppm, less than 500 ppm, less than 250 ppm, less than 100 ppm, less than 75 ppm, from 50 ppm to 100 ppm, from 20 ppm to 1000 ppm, from 20 ppm to 100 ppm, or any subset thereof of vanadium.

The heavy stream 120 may comprise from 40 wt. % to 75 wt. % of naphthenes and aromatics, based on the total weight of hydrocarbons in the heavy stream 120. For example, the heavy stream 120 may comprise from 45 wt. % to 70 wt. %, from 50 wt. % to 65 wt. %, from 55. wt. % to 60 wt. %, or any subset thereof, of naphthenes and aromatics, based on the total weight of hydrocarbons in the heavy stream 120.

The heavy stream 120 may comprise from 15 wt. % to 55 wt. % of polar aromatics, based on the total weight of hydrocarbons in the heavy stream 120. For example, the heavy stream 120 may comprise from 20 wt. % to 50 wt. %, from 25 wt. % to 45 wt. %, from 30 wt. % to 40 wt. %, from 32.5 wt. % to 37.5 wt. %, or any subset thereof, of polar aromatics, based on the total weight of hydrocarbons in the heavy stream 120.

The heavy stream 120 may comprise from 1 wt. % to 12 wt. % of saturated hydrocarbons, based on the total weight of hydrocarbons in the heavy stream 120. For example, the heavy stream 120 may comprise from 2 wt. % to 10 wt. %, from 4 wt. % to 9 wt. %, from 6 wt. % to 8 wt. %, or any subset thereof, of saturated hydrocarbons, based on the total weight of hydrocarbons in the heavy stream 120.

Hydrotreater

The heavy stream 120 may then be hydrotreated 125. Hydrotreating 125 the heavy stream 120 may comprise contacting the heavy stream 120 with one or more hydrotreating catalysts in a hydrotreating system. The hydrotreating system may be a single reactor or a series of reactors directly connected. The heavy stream 120 may be directly introduced into the hydrotreater after fractionating 110.

The heavy stream 120 may be hydrotreated in one or more stages, such as in a three-stage hydrotreater. The multiple stages of the hydrotreater may comprise distinct catalysts in distinct reaction zones. For example, the catalysts may be arranged in distinct beds, the catalysts may be positioned in individual reactors, or the catalysts may be mixed in a single reactor. The heavy stream 120 may contact the one or more hydrotreating catalysts in a down flow manner.

Hydrotreating 125 the heavy stream 120 may comprise exposing the heavy stream 120 to one or more hydrotreating catalysts, such as a hydro-demetallization (also referred to as "HDM") catalyst, a hydro-desulfurization also referred to as "HDS") catalyst, and a hydro-dearomatization (also referred to as "HDA") catalyst. In some embodiments, the one or more hydrotreating catalysts may include hydrodenitrogenation catalysts, hydrodeoxygenation catalysts, or both.

The one or more hydrotreating stages may be arranged in any order. For example, the one or more hydrotreating catalysts may be arranged such that the heavy stream 120 first contacts the HDM catalyst, then the HDS catalyst, then the HDA catalyst. Alternately, the one or more hydrotreating stages may be arranged such that the heavy stream 120 contacts the HDM, then the HDA, then the HDS; or contacts the HDS, HDA, HDM; or contacts the HDS, then the HDM, then the HDA; or contacts the HDA, then the HDS, then the HDM; or contacts the HDA, then the HDM, then the HDS catalyst. Without being limited by theory, it is believed that having the heavy stream 120 contact the HDM and HDS catalysts before the HDA catalysts may prevent or minimize deactivation of the HDA catalysts.

In alternate embodiments, only one or two of the one or more hydrotreating stages and catalysts may be present. The one or more hydrotreating catalysts may be arranged such that the crude oil contacts the HDM then the HDA, or the HDA then the HDM, or the HDS then the HDA, or the HDA then the HDS, or the HDM then the HDS, or the HDS then the HDM catalysts.

In embodiments where the one or more hydrotreating catalysts form a mixed bed, the heavy stream 120 may contact the one or more hydrotreating catalysts in a random or simultaneous manner.

The HDM catalyst may include any catalyst suitable for hydrodemetallization. For example, the HDM catalyst may comprise one or more metals from the Groups 5, 6, or 8-10 of the IUPAC periodic table. In some embodiments, the HDM catalyst may comprise molybdenum. The HDM catalyst may further comprise a support material, and the metal may be disposed on the support material. The support material may be gamma-alumina or silica/alumina extrudates, spheres, cylinders, beads, pellets, and combinations thereof. In some embodiments, the HDM catalyst may comprise a gamma-alumina support, with a surface area of from 100 meters squared per gram ($m^2/g$) to 160 $m^2/g$, such as from 100 $m^2/g$ to 130 $m^2/g$, or from 130 $m^2/g$ to 160 $m^2/g$. In one embodiment, the HDM catalyst may comprise a molybdenum metal catalyst on an alumina support (sometimes referred to as "Mo/$Al_2O_3$ catalyst"). It should be understood throughout this disclosure that metals contained in any of the disclosed catalysts may be present as sulfides or oxides, or even other compounds.

In some embodiments, the HDM catalyst may comprise from 0.5 wt. % to 12 wt. % of an oxide or sulfide of molybdenum, such as from 2 wt. % to 10 wt. % or from 3 wt. % to 7 wt. % of an oxide or sulfide of molybdenum, and from 88 wt. % to 99.5 wt. % of alumina, such as from 90 wt. % to 98 wt. % or from 93 wt. % to 97 wt. % of alumina.

The HDM catalyst may have a relatively large pore volume, such as at least 0.8 cubic centimeters per gram ($cm^3/g$) (for example, at least 0.9 $cm^3/g$, or even at least 1.0 $cm^3/g$). The pore size of the HDM catalyst may be predominantly macro-porous (that is, having a pore size of greater than 50 nanometers (nm)). Without being limited by theory, it is believed that this pore structure and volume may provide a large capacity for the uptake of metals, and optionally dopants, on the surfaces of the HDM catalyst. In one embodiment, the HDM catalyst may include a dopant comprising one or more compounds that include elements selected from the group consisting of boron, silicon, halogens, phosphorus, and combinations thereof.

An exemplary HDM catalyst may include KFR-22 from Albemarle Corp.

The HDS catalyst may comprise one or more metals from the Groups 5, 6, or 8-10 of the IUPAC periodic table. The HDS catalyst may comprise one or more metal from Group 6 and one metal from Groups 8-10 of the IUPAC periodic table. Examples of Group 6 metals include molybdenum and tungsten and examples of Group 8-10 metals include nickel and cobalt. The HDS catalyst may further comprise a support material, and the metal may be disposed on the support material. In some embodiments, the HDS catalyst may comprise Mo and Ni on an alumina support (sometimes referred to as a "Mo—Ni/Al2O3 catalyst"). The HDS catalyst may also contain a dopant that is selected from the group consisting of boron, phosphorus, halogens, silicon, and combinations thereof. In one or more embodiments, the HDS catalyst may comprise from 10 wt. % to 18 wt. % of an oxide or sulfide of molybdenum, such as from 11 wt. % to 17 wt. % or from 12 wt. % to 16 wt. % of an oxide or sulfide of molybdenum, from 1 wt. % to 7 wt. % of an oxide or sulfide of nickel, such as from 2 wt. % to 6 wt. % or from 3 wt. % to 5 wt. % of an oxide or sulfide of nickel, and from 75 wt. % to 89 wt. % of alumina such as from 77 wt. % to 87 wt. % or from 79 wt. % to 85 wt. % of alumina.

The HDS catalyst may have a surface area of 140 m$^2$/g to 200 m$^2$/g, such as from 140 m$^2$/g to 170 m$^2$/g or from 170 m$^2$/g to 200 m$^2$/g. The HDS catalyst may have an intermediate pore volume of from 0.5 cm$^3$/g to 0.7 cm$^3$/g, such as 0.6 cm$^3$/g. The HDS catalyst may generally comprise a mesoporous structure having pore sizes in the range of 12 nm to 50 nm.

An exemplary HDS catalyst may include KFR-33 from Albemarle Corp.

The HDA catalyst may comprise one or more metals from Groups 5, 6, 8, 9, or 10 of the IUPAC periodic table. In some embodiments, the HDA catalyst may comprise one or more metals from Groups 5 or 6 of the IUPAC periodic table, and one or more metals from Groups 8, 9, or 10 of the IUPAC periodic table. In some embodiments, the HDA catalyst may comprise molybdenum or tungsten from Group 6 and nickel or cobalt from Groups 8, 9, or 10. The HDA catalyst may further comprise a support material, such as zeolite, and the metal may be disposed on the support material. In one embodiment, the HDA catalyst may comprise tungsten and nickel metal catalyst on a zeolite support that is mesoporous (sometimes referred to as "W—Ni/meso-zeolite catalyst"). In another embodiment, the HDA catalyst may comprise molybdenum and nickel metal catalyst on a zeolite support that is mesoporous (sometimes referred to as "Mo—Ni/meso-zeolite catalyst"). The zeolite support material may not be limited to any particular type of zeolite. However, it is contemplated that zeolites such as Y, Beta, AWLZ-15, LZ-45, Y-82, Y-84, LZ-210, LZ-25, Silicalite, or mordenite framework zeolites may be suitable for use in the presently-described HDA catalyst.

The support material (such as a mesoporous zeolite) of the HDA catalyst may be characterized as mesoporous by having average pore size of from 2 nm to 50 nm. Without being bound by theory, it is believed that the relatively large-sized pores (that is, mesoporosity) allow for larger molecules to diffuse inside the zeolite, which is believed to enhance the reaction activity and selectivity of the catalyst. Because of the increased pore size, aromatic-containing molecules can more easily diffuse into the catalyst and aromatic cracking may increase. For example, in some conventional embodiments, the feedstock converted by the hydrotreating catalysts may be vacuum gas oils; light cycle oils from, for example, a fluid catalytic cracking reactor; or coker gas oils from, for example, a coking unit. The molecular sizes in these oils are relatively small compared to those of heavy oils such as crude and atmosphere residue, which may be the feedstock of the present methods and systems. The heavy oils generally are unable to diffuse inside the conventional zeolites and be converted on the active sites located inside the zeolites. Therefore, zeolites with larger pore sizes (that is, mesoporous zeolites) may allow the larger molecules of heavy oils to overcome the diffusion limitation, and may promote the reaction and conversion of the larger molecules of the heavy oils.

In one or more embodiments, the HDA catalyst may comprise from 18 wt. % to 28 wt. % of a sulfide or oxide of tungsten, such as from 20 wt. % to 27 wt. % or from 22 wt. % to 26 wt. % of tungsten or a sulfide or oxide of tungsten, from 2 wt. % to 8 wt. % of an oxide or sulfide of nickel, such as from 3 wt. % to 7 wt. % or from 4 wt. % to 6 wt. % of an oxide or sulfide of nickel, and from 5 wt. % to 40 wt. % of mesoporous zeolite, such as from 10 wt. % to 35 wt. % or from 10 wt. % to 30 wt. % of zeolite. In another embodiment, the HDA catalyst may comprise from 12 wt. % to 18 wt. % of an oxide or sulfide of molybdenum, such as from 13 wt. % to 17 wt. % or from 14 wt. % to 16 wt. % of an oxide or sulfide of molybdenum, from 2 wt. % to 8 wt. % of an oxide or sulfide of nickel, such as from 3 wt. % to 7 wt. % or from 4 wt. % to 6 wt. % of an oxide or sulfide of nickel, and from 5 wt. % to 40 wt. % of mesoporous zeolite, such as from 10 wt. % to 35 wt. % or from 10 wt. % to 30 wt. % of mesoporous zeolite.

It should be understood that some embodiments of the presently-described methods and systems may utilize a HDA catalyst that includes a mesoporous zeolite (that is, having an average pore size of from 2 nm to 50 nm). However, in other embodiments, the average pore size of the zeolite may be less than 2 nm (that is, microporous).

An exemplary HDA catalyst may include KFR-70 from Albemarle Corp.

The heavy stream 120 may contact the one or more hydrotreating catalysts at a temperature of at least 300° C., at least 325° C., at least 350° C., at least 375° C., or at least 400° C. The heavy stream 120 may contact the one or more hydrotreating catalysts at a temperature of less than 1000° C., less than 800° C., less than 600° C., less than 500° C., or less than 450° C.

The heavy stream 120 may contact the one or more hydrotreating catalysts in the presence of hydrogen. For example, the atmosphere in which the heavy stream 120 contacts the one or more hydrotreating catalysts may be at least 10 mol. % hydrogen, at least 25 mol. % hydrogen, at least 50 mol. % hydrogen, at least 75 mol. % hydrogen, at least 90 mol. % hydrogen, or even at least 99 mol. % hydrogen.

The heavy stream 120 may contact the one or more hydrotreating catalysts at a pressure of at least 75 bar, at least 100 bar, at least 125 bar, or at least 150 bar. For example, the heavy stream 120 may contact the one or more hydrotreating catalysts at a hydrogen partial pressure of at least 10 bar, at least 20 bar, at least 30 bar, at least 50 bar, at least 75 bar, at least 100 bar, at least 125 bar, or at least 150 bar.

The heavy stream 120 may contact the one or more hydrotreating catalysts at a hydrogen/oil ratio of at least 600. For example, the heavy stream 120 may contact the one or more hydrotreating catalysts at a hydrogen/oil ratio of at least 800, at least 1000, at least 1200, from 600 to 1500, from 800 to 1400, from 1100 to 1300, or any subset thereof.

The heavy stream 120 may contact the one or more hydrotreating catalysts at a liquid hourly space velocity (LHSV) of greater than $0.1\ h^{-1}$, greater than $0.2\ h^{-1}$, greater than $0.25\ h^{-1}$, greater than $0.28\ h^{-1}$, less than $0.5\ h^{-1}$, less than $0.4\ h^{-1}$, less than $0.35\ h^{-1}$, less than $0.32\ h^{-1}$, from $0.1\ h^{-1}$ to $0.5\ h^{-1}$, from $0.2\ h^{-1}$ to $0.4\ h^{-1}$, from $0.25\ h^{-1}$ to $0.35\ h^{-1}$, from $0.28\ h^{-1}$ to $0.32\ h^{-1}$, or any subset thereof Hydrotreated Heavy Stream Hydrotreating 125 the heavy stream 120 may form a hydrotreated heavy stream 130.

At least 50 wt. %, at least 60 wt. %, at least 70 wt. %, at least 80 wt. %, at least 90 wt. %, or even at least 99 wt. % of the hydrotreated heavy stream 130 may have a boiling point temperature of at least 500° C., such as at least 510° C., at least 520° C., at least 530° C., or at least 540° C., based on the total weight of hydrocarbons in the hydrotreated heavy stream 130.

The hydrotreated heavy stream 130 may comprise less than 10 wt. % of sulfur, based on the total weight of hydrocarbons in the hydrotreated heavy stream 130. For example, the hydrotreated heavy stream 130 may comprise less than 8 wt. %, less than 6 wt. %, less than 4 wt. %, less than 2 wt. %, less than 1 wt. %, less than 0.5 wt. %, less than 0.25 wt. %, or even less than 0.1 wt. % of sulfur, based on the total weight of hydrocarbons in the hydrotreated heavy stream 130.

The hydrotreated heavy stream 130 may have a sulfur content of less than 20%, less than 15%, less than 10%, less than 5%, less than 4%, or less than 3%, less than 2%, or even less than 1% of the sulfur content of heavy stream 120. The sulfur content may be measured according to standard test method ASTM D-4924.

The hydrotreated heavy stream 130 may comprise less than 5000 ppm of nitrogen. For example, the hydrotreated heavy stream 130 may comprise less than 2500 ppm, less than 2000 ppm, less than 1500 ppm, less than 1000 ppm, less than 500 ppm, less than 250 ppm, less than 125 ppm, less than 75 ppm, less than 50 ppm, less than 25 ppm, less than 10 ppm, or even less than 1 ppm of nitrogen.

The hydrotreated heavy stream 130 may have a nitrogen content of less than 30%, less than 25%, less than 20%, less than 15%, less than 10%, less than 5%, or even less than 1% of the nitrogen content of the heavy stream 120. The nitrogen content may be measured according to standard test method ASTM D-4629.

The hydrotreated heavy stream 130 may comprise less than 100 ppm of nickel. For example, the hydrotreated heavy stream 130 may comprise less than 75 ppm, less than 50 ppm, less than 25 ppm, less than 15 ppm, less than 10 ppm, less than 5 ppm, or even less than 1 ppm of nickel.

The hydrotreated heavy stream 130 may have a nickel content of less than 30%, less than 25%, less than 20%, less than 15%, less than 10%, less than 5%, or even less than 1% of the nickel content of the heavy stream 120.

The hydrotreated heavy stream 130 may comprise less than 100 ppm of vanadium. For example, the hydrotreated heavy stream 130 may comprise less than 75 ppm, less than 50 ppm, less than 25 ppm, less than 15 ppm, less than 10 ppm, less than 5 ppm, or even less than 1 ppm of vanadium.

The hydrotreated heavy stream 130 may have a vanadium content of less than 30%, less than 25%, less than 20%, less than 15%, less than 10%, less than 5%, or even less than 1% of the vanadium content of the heavy stream 120.

The hydrotreated heavy stream 130 may have an aromatic content of less than 30%, less than 25%, less than 20%, less than 15%, less than 10%, less than 5%, or even less than 1% of the aromatic content of the heavy stream 120.

The hydrotreated heavy stream 130 may have a naphthene and aromatic compound concentration of from 20 wt. % to 55 wt. %, based on the total weight of hydrocarbons in the hydrotreated heavy stream 130. For example, the hydrotreated heavy stream 130 may have a naphthenes and aromatic compound concentration of from 25 wt. % to 50 wt. %, from 30 wt. % to 45 wt. %, from 35 wt. % to 40 wt. %, or any subset thereof, of naphthenes and aromatic compounds, based on the total weight of hydrocarbons in the hydrotreated heavy stream 130.

The hydrotreated heavy stream 130 may have a polar aromatic compound concentration of from 1 wt. % to 6 wt. %, based on the total weight of hydrocarbons in the hydrotreated heavy stream 130. For example, the hydrotreated heavy stream 130 may have a polar aromatic compound concentration of from 2 wt. % to 5 wt. %, from 3 wt. % to 4, wt. %, or any subset thereof, based on the total weight of hydrocarbons in the hydrotreated heavy stream 130.

The hydrotreated heavy stream 130 may comprise from 40 wt. % to 75 wt. % of saturated hydrocarbons, based on the total weight of hydrocarbons in the hydrotreated heavy stream 130. For example, the hydrotreated heavy stream 130 may comprise from 45 wt. % to 70 wt. %, from 50 wt. % to 65 wt. %, from 55 wt. % to 60 wt. %, or any subset thereof, of saturated hydrocarbons, based on the total weight of hydrocarbons in the hydrotreated heavy stream 130.

Combined Feed Stream

The method 100 of processing a hydrocarbon feed 105 may comprise introducing the light stream 115 and the hydrotreated heavy stream 130 to a single FCC reaction zone 140, thereby producing a product stream 145 comprising light olefins.

The light stream 115 and the hydrotreated heavy stream 130 may be introduced directly into to the single FCC reaction zone 140. For example, the light stream 115 and the hydrotreated heavy stream 130 may be combined to form a combined feed stream 135 and the combined feed stream 135 may be fed to the single FCC reaction zone 140. The combined feed stream 135 may comprise at least 80 wt. %, at least 90 wt. %, at least 95 wt. %, at least 99 wt. %, or even at least 99.999 wt. % of the combined weight of the light stream 115 and the hydrotreated heavy stream 130.

The light stream 115 and the hydrotreated heavy stream 130 may be combined to form the combined feed stream 135 in a mixer 150. The mixer 150 may include any device operable to combine two fluids, including high shear mixers, horizontal ribbon mixers, paddle mixers, tumbler mixers, emulsifiers, drum mixers, static mixers, planetary mixers, agitators, and emulsifiers.

Whether light stream 115 and hydrotreated heavy stream 130 are introduced into the single FCC reaction zone separately or in combined feed stream 135, light stream 115 and hydrotreated heavy stream 130 may experience the same degree of severity as one another. For example, light stream 115 and hydrotreated heavy stream 130 may experience peak temperatures within 10° C., within 5° C., within 2.5° C., within 1° C., or even within 0.1° C. of one another; residence times within 90%, within 95%, within 99%, or even within 99.99% of one another; or both.

FCC Operating Conditions

In some embodiments, the FCC reaction zone may be operated in a down-flow manner. Without being limited by theory, it is believed that because reactants and catalysts travel together down a reaction zone in a down-flow FCC, the spatial variation in severity, residence time, and temperature is greater than in an up-flow or FCC.

A down-flow FCC reactor or "downer" is one in which the reactants flow from a catalyst/feed mixing zone downward through the cracking reaction zone to a separation zone. The hydrocarbons are reacted by contact with the FCC catalyst composition in the cracking reaction zone, which causes at least a portion of the hydrocarbons to undergo one or more cracking reactions to form one or more cracking reaction products, such as light olefins. The catalyst, which may have a temperature equal to or greater than the reaction temperature of the cracking reaction zone, may transfer heat to the hydrocarbons, thereby promoting the endothermic cracking reaction.

Steam may be introduced to the top portion of the cracking reaction zone to provide additional heating to the mixture of hydrocarbons and catalyst. Steam may additionally function as a diluent, reducing the partial pressure of hydrocarbons in the FCC reactor. Steam may also prevent secondary reactions, serving to increase selectivity of the cracking reactions.

Upon exit from the FCC reactor, the catalyst may be separated from the hydrocarbons to isolate a spent catalyst. The spent catalyst may then be sent to a regenerator. Regenerated catalyst may have an activity greater than the spent catalyst.

The single FCC reaction zone 140 may be operated under high-severity conditions, otherwise known as an HS-FCC. The single FCC reaction zone 140 may be operated at a peak temperature of greater than or equal to 580° C., a weight ratio of the FCC catalyst composition to the crude oil of from 2:1 to 10:1, and a residence time of from 0.1 seconds to 60 seconds.

The single FCC reaction zone 140 may operate at a peak temperature of greater than or equal to 580° C. For example, the FCC system may operate at a peak temperature of greater than 600° C., greater than 620° C., greater than 640° C., greater than 645° C., greater than 660° C., greater than 670° C., from 600 to 700° C., from 600 to 690° C., from 600 to 680° C., from 650 to 700° C., from 650 to 690° C., from 650 to 680° C., from 670 to 700° C., from 670 to 680° C., or any subset thereof. When the reaction temperature is greater than, for instance, 720° C. or 700° C., the hydrocarbons may undergo increased thermal cracking and decreased catalytic cracking compared to embodiments where the reaction temperature is less than 720° C. or 700° C. Without being limited by theory, it is believed that thermal cracking of the hydrotreated effluent can increase yield of ethylene and decrease yield of other products. Catalytic cracking of the hydrocarbons in the single FCC reaction zone 140 can yield a greater quantity of desired products, such as light olefins and aromatics.

The weight ratio of the FCC catalyst composition to hydrocarbons in the single FCC reaction zone 140 may be from 2:1 to 10:1, such as from 2:1 to 8:1, from 2:1 to 6:1, from 2:1 to 4:1, from 4:1 to 10:1, from 6:1 to 10:1, or from 8:1 to 10:1. It should be understood that as used in this paragraph, "hydrocarbons" refers to the combined hydrocarbons of the light stream 115 and the hydrotreated heavy stream 130.

The fluid catalytic cracking system may be operated with a catalyst-to-oil weight (CTO) ratio from 2:1 to 10:1, where the catalyst-to-oil weight ratio is the weight ratio of the FCC catalyst composition to the weight of hydrocarbons in a unit volume of the reaction mixture comprising the light stream 115, the hydrotreated heavy stream 130, and the FCC catalyst composition. For example, the single FCC reaction zone 140 can be operated with a catalyst-to-oil weight ratio from 2:1 to 3:1, from 2:1 to 5:1, from 2:1 to 10:1, from 3:1 to 5:1, or from 5:1 to 10:1. Without being bound by theory, it is believed that a catalyst-to-oil weight ratio less than 2:1 may not provide a sufficient amount of catalyst present to catalytically crack the hydrocarbons at an economically high yield. It is believed that a catalyst-to-oil weight ratio greater than 10:1 may not be economically practical for scaling up in commercial applications.

The hydrocarbons may contact the FCC catalyst composition in the single FCC reaction zone 140 with a residence time of from 0.1 to 60 seconds. For example, the hydrocarbons may contact the FCC catalyst composition with a residence time of from 5 to 60 seconds, from 10 to 60 seconds, from 20 to 60 seconds, from 30 to 60 seconds, from 40 to 60 seconds, from 50 to 60 seconds, from 0.1 to 50 seconds, from 0.1 to 40 seconds, from 0.1 to 30 seconds, from 0.1 to 20 seconds, from 0.1 to 10 seconds, from 10 to 50 seconds, from 20 to 40 seconds, or any subset thereof. Without intending to be bound by any particular theory, it is believed that a residence time less than 0.1 seconds may not provide sufficient time for hydrocarbons to be sufficiently cracked by the FCC catalyst composition.

The hydrocarbons may contact the FCC catalyst composition in the presence of steam. For example, the ratio of hydrocarbon to FCC catalyst composition may be steam to hydrocarbons may be from 0:1 to 1:1, such as from 0:1 to 0.75:1, from 0:1 to 0.5:1, from 0:1 to 0.25:1, from 0:1 to 0.1:1, from 0:1 to 0.01:1, or any subset thereof.

The FCC catalyst composition may include one or more of a variety of fluid catalytic cracking catalysts, which may be suitable for use in the single FCC reaction zone 140 operated at high severity conditions. Examples of fluid catalytic cracking catalysts suitable for use as the FCC catalyst composition may include, without limitation, zeolites, silica-alumina catalysts, carbon monoxide burning promoter additives, bottoms cracking additives, light olefin-producing additives, other catalyst additives, or combinations of these components. Zeolites that may be used as at least a portion of the FCC catalyst composition for cracking may include, but are not limited to Y, REY, USY, RE-USY zeolites, or combinations of these. The FCC catalyst composition may also include a shaped selective catalyst additive, such as ZSM-5 zeolite crystal or other pentasil-type catalyst structures, which are often used in other FCC processes to produce light olefins and/or increase FCC gasoline octane. In one or more embodiments, the FCC catalyst composition may include a mixture of a ZSM-5 zeolite crystal and the cracking catalyst zeolite and matrix structure of a conventional FCC cracking catalyst. In one or more embodiments, the FCC catalyst composition may be a mixture of Y and ZSM-5 zeolite catalysts embedded with clay, alumina, and binder.

In one or more embodiments, at least a portion of the FCC catalyst composition may be modified to include one or more rare earth elements (15 elements of the Lanthanide series of the IUPAC Periodic Table plus scandium and yttrium), alkaline earth metals (Group 2 of the IUPAC Periodic Table), transition metals, phosphorus, fluorine, or any combination of these, which may enhance olefin yield. Transition metals may include "an element whose atom has a partially filled d sub-shell, or which can give rise to cations with an incomplete d sub-shell" [IUPAC, Compendium of Chemical Terminology, 2nd ed. (the "Gold Book") (1997). Online corrected version: (2006—) "transition element"]. One or more transition metals or metal oxides may also be impregnated onto the catalyst. Metals or metal oxides may include one or more metals from Groups 6-10 of the IUPAC Periodic Table. The metals or metal oxides may include one or more of molybdenum, rhenium, tungsten, or any combination of these. At least a portion of the FCC catalyst composition may be impregnated with tungsten oxide.

The FCC catalyst composition may be formed by a variety of processes. According to one embodiment, the matrix material can be mixed with a fluid such as water to form a slurry, and the zeolites can be separately mixed with a fluid such as water to form a slurry. The matrix material slurry and the zeolite slurry can be combined under stirring. Separately, another slurry can be formed by combining the binder material with a fluid such as water. The binder slurry can then be combined with the slurry containing the zeolites and matrix material to form a final slurry. The final slurry can then be dried, for example by spraying, and then calcined to produce the microparticles of the cracking catalyst.

The FCC catalyst composition can be in the form of shaped microparticles, such as microspheres. As used in the present disclosure, "microparticles" refer to particles having an average particle size of from 0.1 microns and 100 microns. The size of a microparticle refers to the maximum length of a particle from one side to another, measured along the longest distance of the microparticle. For instance, a spherically shaped microparticle has a size equal to its diameter, or a rectangular prism shaped microparticle has a maximum length equal to the hypotenuse stretching from opposite corners. In embodiments, each zeolitic component of the FCC catalyst composition can be included in each catalyst microparticle. However, in other embodiments, microparticles can be mixed, where the microparticles contain only a portion of the FCC catalyst composition. For instance, a mixture of two microparticle types may be included in the FCC catalyst composition, where one type of microparticle includes only ZSM-5, and another type of microparticle includes only the USY zeolite.

The FCC catalyst composition can be contacted with steam prior to use in the single FCC reaction zone 140. The purpose of steam treatment can be to accelerate the hydrothermal aging of the FCC catalyst composition that occurs during operation of the FCC system to obtain an equilibrium catalyst. Not intending to be bound by any particular theory, it is believed that the steam treatment can lead to the removal of aluminum from the framework leading to a decrease in the number of sites where framework hydrolysis can occur under hydrothermal and thermal conditions. This removal of aluminum results in an increased thermal and hydrothermal stability in dealuminated zeolites. The unit cell size can decrease as a result of dealumination, since the smaller $SiO_4$ tetrahedron replaces the larger $AlO_4^-$ tetrahedron. The acidity of zeolites can also be affected by dealumination through the removal of framework aluminum and the formation of extra-framework aluminum species. Dealumination may affect the acidity of the zeolites by decreasing the total acidity and increasing the acid strength of the zeolite. The total acidity can decrease because of the removal of framework aluminum, which act as Brønsted acid sites. The acid strength of the zeolite may be increased because of the removal of paired acid sites or the removal of the second coordinate next nearest neighbor aluminum. The increase in the acid strength may be caused by the charge density on the proton of the OH group being highest when there is no framework aluminum in the second coordination sphere. In embodiments, the FCC catalyst composition can be contacted with steam at a temperature greater than or equal to 800° C. for a period of 6 hours or greater prior to contacting the hydrocarbons with the FCC catalyst composition.

In embodiments, one or more supplemental feed streams can be combined with the hydrocarbons before introduction of the hydrocarbons to the FCC catalyst. The one or more supplemental feed streams may be added such that they contact the FCC catalyst simultaneously with the hydrocarbons of the light stream, middle stream, heavy stream, and hydrotreated residue streams. The supplemental feed stream may include one or more of vacuum residues, tar sands, bitumen, atmospheric residues, vacuum gas oils, demetalized oils, naphtha streams, or combinations of these.

Product Stream

Fluid catalytic cracking of the light stream 115 and the hydrotreated heavy stream 130 in the single FCC reaction zone 140 may produce a product stream 145 comprising light olefins. "Light olefins" refers to compounds which include at least one carbon-carbon double bond and from two to four carbon atoms. The cracked effluent may comprise at least 15 wt. %, at least 20 wt. %, at least 25 wt. %, at least 30 wt. %, at least 35 wt. %, at least 36 wt. %, at least 37 wt. % or at least 38 wt. % of light olefins.

The product stream 145 may comprise at least 2 wt. % of $C_2$ olefins, such as ethylene. For example, the product stream 145 may comprise at least 4 wt. %, at least 6 wt. %, at least 8 wt. %, at least 10 wt. %, or at least 10.5 wt. % of $C_2$ olefins.

The product stream 145 may comprise at least 2 wt. % of $C_3$ olefins, such as propylene. For example, the product stream 145 may comprise at least 5 wt. %, at least 10 wt. %, at least 15 wt. %, at least 17 wt. %, or at least 18 wt. % of $C_3$ olefins.

The product stream 145 may comprise at least 2 wt. % of $C_4$ olefins, such as butenes. For example, the product stream 145 may comprise at least 5 wt. %, at least 8 wt. %, at least 9 wt. % of $C_4$ olefins.

The product stream 145 may comprise at least 5 wt. % of gasoline range products. For example, the product stream 145 may comprise at least 10 wt. %, at least 20 wt. %, at least 25 wt. %, or at least 27 wt. % of gasoline range products.

Fluid catalytic cracking of the light stream 115 and the hydrotreated heavy stream 130 in the single FCC reaction zone 140 may convert the hydrocarbons originally found in the hydrocarbon feed 105 to other products. For example, fluid catalytic cracking of the light stream 115 and the hydrotreated heavy stream 130 in the single FCC reaction zone 140 may convert at least 50 wt. %, at least 60 wt. %, at least 70 wt. %, at least 80 wt. %, at least 88 wt. %, at least 89 wt. %, or even at least 90 wt. % of the hydrocarbons originally in the hydrocarbon feed 105 to other products, such as light olefins.

Fluid catalytic cracking of the light stream 115 and the hydrotreated heavy stream 130 in the single FCC reaction zone 140 may convert a portion of the hydrocarbons originally found in the hydrocarbon feed 105 to coke. Coke is a solid residue created when oil undergoes severe oxidative and thermal breakdown. Coke may be deposited on the catalyst, the reactor surfaces, or both. In either location, coke may foul the surfaces, impeding reactions. Contacting the above streams with the catalyst may convert less than 13 wt. %, less than 12 wt. %, less than 11 wt. %, or less than 10 wt. % of the hydrocarbons originally in the hydrocarbon feed 105 to coke.

EXAMPLES

The various aspects of the present disclosure will be further clarified by the following examples. The examples are illustrative in nature and should not be understood to limit the subject matter of the present disclosure.

Example 1

An Arab light crude oil with an API gravity of 33.0 and a sulfur content of 1.6 wt. % was fractionated in a distillation column to form a light stream and a heavy stream. Properties of the feed crude oil stream and the resulting fractions (based on their wt. % composition in the crude oil) are given in Table 1 below.

TABLE 1

| Stream Name | Boiling Range | Ni (ppm) | V (ppm) | S (wt. %) | N (ppm) |
|---|---|---|---|---|---|
| Hydrocarbon Feed | | 4.4 | 14.2 | 1.6 | 444 |
| Light Stream | Less than 540° C. | <1 | <1 | 0.8 | 136 |
| Heavy Stream | Greater than 540° C. | 4.4 | 14.2 | 0.8 | 308 |

Example 2

The heavy stream from Example 1 was hydrotreated in a three-stage hydrotreater. The reaction conditions were: a weighted average bed temperature of 400° C., a pressure of 150 bar, a liquid hourly space velocity (LHSV) of 0.5 h$^{-1}$, an H$_2$/oil ratio 1200:1 (v/v), an oil flowrate of 300 ml/h, and an H$_2$ flowrate of 360 L/h.

The first stage of the hydrotreater used a KFR-22 catalyst from Albemarle Co. to accomplish hydro-demetallization (HDM). The second stage of the hydrotreater used a KFR-33 catalyst from Albemarle Co. to accomplish hydro-desulfurization (HDS). The third stage of the hydrotreater used a KFR-70 catalyst from Albemarle Co. to accomplish hydro-dearomatization (HDA). The first, second, and third stages were discrete beds placed atop one another in a single reaction zone. The heavy stream flowed downward to the first stage, then to the second stage, and then to the third stage. Properties of this hydrotreated heavy stream are shown in Table 2 below.

TABLE 2

| Kinematic viscosity at 100° C. | 67.6 mm$^2$/s |
|---|---|
| Density at 60° C. | 0.9 g/cm$^3$ |
| Sulfur (wt. %) | 0.36 |
| Ni (ppm) | 1 |
| V (ppm) | 3 |
| Fe (ppm) | <1 |
| Na (ppm) | <10 |

Example 3

A catalyst with the composition shown in Table 3 below as used in all of the reactions.

TABLE 3

| Component | Weight % | Notes |
|---|---|---|
| ZSM-5 | 20 | Phosphorus impregnated at 7.5 wt. % P$_2$O$_5$ on zeolite |
| USY | 21 | Lanthanum impregnated at 2.5 wt. % La$_2$O$_3$ on zeolite |
| Alumina | 8 | Pural SB from Sasol |
| Clay | 49 | Kaolin |
| Silica | 2 | Added as colloidal silica Ludox TM-40 |

An Advanced Cracking Evaluation (ACE) unit was used to simulate a down-flow FCC reaction zone with multiple inlet points. The ACE unit emulates commercial FCC process.

Prior to each experiment, the catalyst is loaded into the reactor and heated to the desired reaction temperature. N$_2$ gas is fed through the feed injector from the bottom to keep catalyst particles fluidized. Once the catalyst bed temperature reaches within ±2° C. of the reaction temperature, the reaction can begin. Feed is then injected for a predetermined time (time-on-stream (TOS)). The desired catalyst-to-feed ratio is obtained by controlling the feed pump. The gaseous product is routed to the liquid receiver, where C$_{5+}$ hydrocarbons are condensed and the remaining gases are routed to the gas receiver. After catalyst stripping is over, the reactor is heated to 700° C., and nitrogen was replaced with air to regenerate the catalyst. During regeneration, the released gas is routed to a CO$_2$ analyzer. Coke yield is calculated from the flue gas flow rate and CO2 concentration. The above process was repeated for each of Examples 3(A) and 3(B).

Example 3 (EX-3)

The light stream from Example 1 was combined with the hydrotreated heavy stream from Example 2 to form a combined feed stream. The combined feed stream was fed to the ACE unit. A time-on-stream (TOS) of 75 seconds and a temperature of 675° C. was used. Fresh catalyst was steamed deactivated at 810° C. for 6 hours to resemble the equilibrium catalyst in the actual process. The steam deactivated catalyst was used in this reaction. It should be understood that TOS is directly proportional to residence time.

Comparative Example 1 (CE-1)

The same Arab light crude oil used in Example 3 was directly cracked in the same cracking reactor and under the same conditions as was used in Example 3.

TABLE 4

| Constituent | EX-3 (wt. %) | CE-1 (wt. %) |
|---|---|---|
| H2 | 0.68 | 0.72 |
| C$_1$ | 6.47 | 6.86 |
| C$_2$ | 3.10 | 3.23 |
| C$_2$ = (ethylene) | 10.85 | 10.41 |
| C$_3$ | 1.67 | 1.65 |
| C$_3$ = (propylene) | 18.20 | 16.51 |
| iC$_4$ | 0.46 | 0.42 |
| nC4 | 0.41 | 0.56 |
| t2C$_4$ = | 2.22 | 1.93 |
| 1C$_4$ = | 1.65 | 1.40 |
| iC$_4$ = | 3.57 | 3.09 |
| c2C$_4$ = | 1.79 | 1.54 |
| 1,3-BD | 1.11 | 0.99 |
| Butenes | 9.22 | 7.96 |
| Total Gas | 52.17 | 49.31 |

TABLE 4-continued

| Constituent | EX-3 (wt. %) | CE-1 (wt. %) |
|---|---|---|
| Dry Gas | 10.24 | 10.80 |
| Total Light Olefins | 38.27 | 34.89 |
| Gasoline | 27.92 | 24.21 |
| LCO | 8.43 | 9.43 |
| HCO | 2.04 | 3.20 |
| Coke | 9.44 | 13.86 |
| Total Gas + Coke | 61.61 | 63.17 |

As can be seen in Table 4, the yield of total light olefins from the inventive EX-3 is significantly higher than the yield of light olefins in the comparative CE-1. Additionally, EX-3 shows significantly lower coke formation than the comparative CE-1.

ASPECTS

According to a first aspect of the present disclosure, a method of processing a hydrocarbon feed comprises fractionating the hydrocarbon feed into a light stream and a heavy stream, wherein the light stream comprises hydrocarbons boiling at less than 540° C. and the heavy stream comprises hydrocarbons boiling at greater than 540° C.; hydrotreating the heavy stream to form a hydrotreated heavy stream; combining the light stream and the hydrotreated heavy stream to form a upgraded feed stream; feeding the upgraded feed stream to a single Fluid Catalytic Cracking (FCC) reaction zone, thereby producing a product stream comprising light olefins; the FCC reaction zone is operated in a down-flow configuration; and the FCC is operated under high severity conditions.

According to a second aspect of the present disclosure, in conjunction with the first aspect, the FCC reaction zone operates at a temperature of greater than or equal to 580° C., a weight ratio of an FCC catalyst composition to the crude oil of from 2:1 to 10:1, and a residence time of from 0.1 seconds to 60 seconds.

According to a third aspect of the present disclosure, in conjunction with any of the first or second aspects, the heavy stream is hydrotreated in a three stage hydrotreater.

According to a fourth aspect of the present disclosure, in conjunction with any of the first through third aspects, hydrotreating the heavy stream comprises exposing the heavy stream to a hydro-demetallization catalyst, a hydro-desulfurization catalyst, and a hydro-dearomatization catalyst.

According to a fifth aspect of the present disclosure, in conjunction with any of the first through fourth aspects, hydrotreating the heavy stream comprises exposing the heavy stream to a hydro-demetallization catalyst, then a hydro-desulfurization catalyst, and then a hydro-dearomatization catalyst.

According to a sixth aspect of the present disclosure, in conjunction with any of the first through fifth aspects, the feed stream is a whole crude oil.

According to a seventh aspect of the present disclosure, in conjunction with any of the first through sixth aspects, the feed stream has an API gravity of from 25 to 35.

According to an eighth aspect of the present disclosure, in conjunction with any of the first through seventh aspects, the light stream comprises at least 80 wt. % of hydrocarbons boiling at less than 540° C., based on the total weight of hydrocarbons in the light stream.

According to a ninth aspect of the present disclosure, in conjunction with any of the first through eighth aspects, the heavy stream comprises at least 80 wt. % of hydrocarbons boiling at greater than 540° C., based on the total weight of hydrocarbons in the heavy stream.

According to a tenth aspect of the present disclosure, in conjunction with any of the first through ninth aspects, the heavy stream comprises less than 3 wt. % sulfur, based on the total weight of hydrocarbons in the heavy stream.

According to an eleventh aspect of the present disclosure, in conjunction with any of the first through tenth aspects, the feed stream is an Arab Heavy, Arab Medium, Arab Light, or Arab Extra Light crude oil.

According to a twelfth aspect of the present disclosure, in conjunction with any of the first through eleventh aspects, the product stream comprising light olefins comprises at least 35 wt. % of light olefins, based on the total weight of hydrocarbons in the product stream.

According to a thirteenth aspect of the present disclosure, in conjunction with any of the first through twelfth aspects, the product stream comprising light olefins comprises at least 17 wt. % of propylene, based on the total weight of hydrocarbons in the product stream.

According to a fourteenth aspect of the present disclosure, in conjunction with any of the first through thirteenth aspects, the product stream comprising light olefins comprises at least 8 wt. % of butenes.

According to a fifteenth aspect of the present disclosure, in conjunction with any of the first through fourteenth aspects, contacting the feeding the upgraded feed stream to the single FCC reaction zone convers less than 11 wt. % of the upgraded feed stream to coke.

According to a sixteenth aspect of the present disclosure, in conjunction with any of the first to fifteenth aspects, the light stream comprises at least 99 wt. % of hydrocarbons originally in the hydrocarbon feed which boil at a temperature of less than 540° C.

According to a seventeenth aspect of the present disclosure, in conjunction with any of the first through sixteenth aspects, the heavy stream comprises at least 99 wt. % of hydrocarbons originally in the hydrocarbon feed which boil at a temperature of greater than 540° C.

According to an eighteenth aspect of the present disclosure, in conjunction with any of the first through seventeenth aspects, the hydrocarbon feed is a whole crude oil; the light stream comprises at least 99 wt. % of hydrocarbons boiling at less than 540° C., based on the total weight of hydrocarbons in the light stream; the light stream comprises at least 99 wt. % of all hydrocarbons initially in the hydrocarbon feed which boil at less than 540° C.; the heavy stream comprises at least 99 wt. % of hydrocarbons boiling at greater than 540° C., based on the total weight of hydrocarbons in the heavy stream; the heavy stream comprises at least 99 wt. % of all hydrocarbons initially in the hydrocarbon feed which boil at greater than 540° C.; hydrotreating the heavy stream comprises contacting the heavy stream with a hydro-demetallization catalyst, a hydro-desulfurization catalyst, and a hydro-dearomatization catalyst in the presence of hydrogen.

It is noted that any two quantitative values assigned to a property may constitute a range of that property, and all combinations of ranges formed from all stated quantitative values of a given property are contemplated in this disclosure.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

Having described the subject matter of the present disclosure in detail and by reference to specific aspects, it is noted that the various details of such aspects should not be taken to imply that these details are essential components of the aspects. Rather, the claims appended hereto should be taken as the sole representation of the breadth of the present disclosure and the corresponding scope of the various aspects described in this disclosure. Further, it will be apparent that modifications and variations are possible without departing from the scope of the appended claims.

The invention claimed is:

1. A method of processing a hydrocarbon feed comprising fractionating the hydrocarbon feed into a light stream and a heavy stream, wherein the light stream comprises hydrocarbons boiling at less than 540° C. and the heavy stream comprises hydrocarbons boiling at greater than 540° C.;
hydrotreating the heavy stream to form a hydrotreated heavy stream;
combining the light stream and the hydrotreated heavy stream to form an upgraded feed stream;
feeding the upgraded feed stream to a single Fluid Catalytic Cracking (FCC) reaction zone, thereby producing a product stream comprising light olefins
the FCC reaction zone is operated in a down-flow configuration; and
the FCC reaction zone is operated under high severity conditions.

2. The method of claim 1, wherein the FCC reaction zone operates at a temperature of greater than or equal to 580° C., a weight ratio of the FCC catalyst composition to the hydrocarbon feed of from 2:1 to 10:1, and a residence time of from 0.1 seconds to 60 seconds.

3. The method of claim 1, wherein the heavy stream is hydrotreated in a three stage hydrotreater.

4. The method of claim 1, wherein hydrotreating the heavy stream comprises exposing the heavy stream to a hydro-demetallization catalyst, a hydro-desulfurization catalyst, and a hydro-dearomatization catalyst.

5. The method of claim 1, wherein hydrotreating the heavy stream comprises exposing the heavy stream to a hydro-demetallization catalyst, then a hydro-desulfurization catalyst, and then a hydro-dearomatization catalyst.

6. The method of claim 1, wherein the feed stream is a whole crude oil.

7. The method of claim 1, wherein the feed stream has an API gravity of from 25 to 35.

8. The method of claim 1, wherein the light stream comprises at least 80 wt. % of hydrocarbons boiling at less than 540° C., based on the total weight of hydrocarbons in the light stream.

9. The method of claim 1, wherein the heavy stream comprises at least 80 wt. % of hydrocarbons boiling at greater than 540° C., based on the total weight of hydrocarbons in the heavy stream.

10. The method of claim 1, wherein the heavy stream comprises less than 3 wt. % sulfur, based on the total weight of hydrocarbons in the heavy stream.

11. The method of claim 1, wherein the product stream comprising light olefins comprises at least 35 wt. % of light olefins, based on the total weight of hydrocarbons in the product stream.

12. The method of claim 1, wherein the product stream comprising light olefins comprises at least 17 wt. % of propylene, based on the total weight of hydrocarbons in the product stream.

13. The method of claim 1, wherein the product stream comprising light olefins comprises at least 8 wt. % of butenes.

14. The method of claim 1, wherein contacting the feeding the upgraded feed stream to the single FCC reaction zone convers less than 11 wt. % of the upgraded feed stream to coke.

15. The method of claim 1, wherein the light stream comprises at least 99 wt. % of hydrocarbons originally in the hydrocarbon feed which boil at a temperature of less than 540° C.

16. The method of claim 1, wherein the heavy stream comprises at least 99 wt. % of hydrocarbons originally in the hydrocarbon feed which boil at a temperature of greater than 540° C.

17. The method of claim 1, wherein;
the hydrocarbon feed is a whole crude oil;
the light stream comprises at least 99 wt. % of hydrocarbons boiling at less than 540° C., based on the total weight of hydrocarbons in the light stream;
the light stream comprises at least 99 wt. % of all hydrocarbons initially in the hydrocarbon feed which boil at less than 540° C.;
the heavy stream comprises at least 99 wt. % of hydrocarbons boiling at greater than 540° C., based on the total weight of hydrocarbons in the heavy stream;
the heavy stream comprises at least 99 wt. % of all hydrocarbons initially in the hydrocarbon feed which boil at greater than 540° C.;
hydrotreating the heavy stream comprises contacting the heavy stream with a hydro-demetallization catalyst, a hydro-desulfurization catalyst, and a hydro-dearomatization catalyst in the presence of hydrogen.

* * * * *